United States Patent [19]
Lai

[11] Patent Number: 5,907,594
[45] Date of Patent: May 25, 1999

[54] RECONSTRUCTION OF VOLUMETRIC IMAGES BY SUCCESSIVE APPROXIMATION IN CONE-BEAM COMPUTED TOMOGRAPHY SYSTEMS

[75] Inventor: Ching-Ming Lai, Wakefield, Mass.

[73] Assignee: Analogic Corporation, Peabody, Mass.

[21] Appl. No.: 09/066,494

[22] Filed: Apr. 24, 1998

Related U.S. Application Data

[60] Provisional application No. 60/051,409, Jul. 1, 1997.
[51] Int. Cl.[6] .................................................. A61B 6/03
[52] U.S. Cl. ................... 378/4; 378/15; 378/901
[58] Field of Search .................. 378/4, 15, 901

[56] References Cited

U.S. PATENT DOCUMENTS

| | | | |
|---|---|---|---|
| 5,229,934 | 7/1993 | Mattson et al. | 600/425 |
| 5,253,171 | 10/1993 | Hsiao et al. | 378/4 |
| 5,291,402 | 3/1994 | Pfoh | 378/13 |
| 5,377,250 | 12/1994 | Hu | 378/15 |
| 5,414,623 | 5/1995 | Lu et al. | 382/131 |
| 5,430,785 | 7/1995 | Pfoh et al. | 378/19 |
| 5,438,602 | 8/1995 | Crawford et al. | 378/4 |

OTHER PUBLICATIONS

L.A. Feldkamp, L.C. Davis, and J.W. Kress, "Practical Cone–beam Algorithm," J. Opt. Soc. Am. A, vol. 1, p. 612, No. 6, Jun. 1984.

D.L. Parker, "Optimal Short Scan Convolution Reconstruction for Fan beam CT," Med. Phys., vol. 9, No. 2, p.254, Mar./Apr., 1982.

*Primary Examiner*—David P. Porta
*Assistant Examiner*—David Vernon Bruce
*Attorney, Agent, or Firm*—Lappin & Kusmer LLP

[57] ABSTRACT

In an improved method and apparatus for cone-beam reconstruction, a technique for mitigating reconstruction error, referred to herein as successive approximation, incrementally improves the quality of the resultant image, with an exponential decrease in error at each succession. Projection data are collected and reconstructed to form a first reconstructed image containing error due to imprecision in reconstruction. The first reconstructed image is forward projected to generate intermediate projection data which are in turn compared to the collected projection data to generate error projection data. The error projection data are reconstructed to form an error image which is, in turn, used to correct the first reconstructed image. The result is a second image which is improved in image quality. The invention is applicable to a range of computed tomography applications, including medical scanning, baggage scanning, and industrial product scanning applications.

57 Claims, 4 Drawing Sheets

RECONSTRUCTION OF VOLUMETRIC IMAGES BY SUCCESSIVE APPROXIMATION IN CONE-BEAM COMPUTED TOMOGRAPHY SYSTEMS

RELATED APPLICATION

This application claims the benefit of U.S. Provisional Application No. 60/051,409, filed Jul. 1, 1997, the contents of which are incorporated herein by reference.

BACKGROUND OF THE INVENTION

In modern computed tomography (CT) scanner systems, an X-ray source generates an X-ray beam which interrogates an object and is incident on a sensor array. In third-generation CT systems, the source and sensor array are mounted on a gantry which rotates about the object. Successive sets of projections of the object are recorded at incremental gantry rotation angles. After completion of a half rotation of the gantry ("half-scan" system) or a full rotation ("full-scan" system), data from the successive rotation angles are combined in a process known as reconstruction to create a cross-sectional image of the object. In a stationary scan configuration, the object is fixed in position during each scan, while in a translational scan, or "helical" scan, the object translates relative to the gantry during a scan, improving system throughput, but complicating image reconstruction.

In a conventional two-dimensional CT scanner of the third generation type, the X-ray beam propagates in a planar fan shape between a point source and a sensor array comprising a one-dimensional array of detector elements. The fan beam is referred to as a "transaxial fan" because the plane of the fan is perpendicular to the rotation axis, i.e., the z-axis. A two-dimensional image reconstruction process collects the raw data at each rotation angle and following a half-scan, or full-scan, converts the data into a planar pixel image of the portion of the object through which the X-rays have passed. Following each scan, the object may be translated along the z-axis to generate adjacent planar cross-sectional images or "slices" of the object which can be combined to produce a volumetric image.

To speed up volumetric imaging of the object, a three-dimensional CT scanner employs a conical X-ray beam, also referred to as "cone beam", generated at a point source, which projects through the object and is incident on a two-dimensional sensor array. The array typically comprises multiple rows and multiple columns of detectors which lie on a cylindrical surface. In this configuration, the X-ray cone beam diverges not only along the plane of the transaxial fan, but also diverges along the z-axis.

In practice, a conventional two-dimensional reconstruction algorithm is insufficient for reconstructing a three-dimensional volumetric image from cone-beam data collected with a two-dimensional detector array. The three-dimensional cone-beam data cannot be accurately resolved into independent parallel layers along the z-axis for introduction into two-dimensional reconstruction since each transaxial fan (defined as the portion of a conical beam passing through a corresponding row of detectors) lies at a conical angle relative to the z-axis that varies from one detector to the next. Performing two-dimensional reconstruction using this data would therefore result in reconstruction errors for each set of fan beam data, with the exception of the central transaxial fan along the xy-plane (where the plane of the transaxial fan is normal to the z-axis). The reconstruction errors worsen as the conical angle increases from the zero angle defined by the central transaxial fan. A more accurate three-dimensional reconstruction technique known as cone-beam reconstruction for stationary scan configurations is described in:

1. L. A. Feldkamp, L. C. Davis, and J. W. Kress, "Practical Cone-beam Algorithm", J. Opt. Soc. Am. A, Vol.1, p612, No.6, June 1984.

The foregoing discussion applies to scanning an object which is stationary with respect to the z-axis. In another form of scanning, known in the art as a helical scan, the object translates relative to the gantry along a translation axis, usually parallel to the z-axis, at a constant speed during gantry rotation. From the perspective of the object, the x-ray source and sensors can be envisioned as circling about the object in a helical trajectory during data collection. In a helical scan performed by a conventional system having a single row of detectors, the projection data are first interpolated to the z position of each slice for generating its planar image. These planar images are located contiguously along the z-axis. The contiguous slices can be combined and further processed for various modes of three-dimensional display. Unfortunately, in a cone-beam system, the z-axis translation causes the collected data to deviate further from that data which is required for standard two-dimensional or three-dimensional reconstruction techniques. As a result, the reconstruction errors arising from a helical scan using a cone-beam system are worse than that of a stationary scan. Reconstruction and enhancement methods for cone-beam helical scans are described in:

2. U.S. Pat. No. 5,291,402 issued Mar. 1, 1994, to A. H. Pfoh, "Helical Scanning Computed Tomography Apparatus";

3. U.S. Pat. No. 5,377,250 issued Dec. 27, 1994, to H. Hu,"Reconstruction Method for Helical Scanning Computed Tomography Apparatus with Multi-row Detector Array"; and 4. U.S. Pat. No. 5,430,783 issued Jul. 4, 1995, to H. Hu, N. J. Pele, and A. H. Pfoh, "Reconstruction Method for Helical Scanning Computed Tomography Apparatus with Multi-row Detector Array Employing Overlapping Beams".

SUMMARY OF THE INVENTION

The present invention is directed to an apparatus and method for reducing imaging errors arising from reconstruction of images in a computed tomography system. A successive process incrementally improves the quality of the resultant image, with an exponential decrease in error at each succession. The technique, referred to herein as "successive approximation", is especially attractive for cone-beam helical systems, but is equally applicable to conventional helical and fixed-axis scanning systems.

Projection data are collected and reconstructed to form a first reconstructed image. The first reconstructed image is forward projected to generate intermediate projection data. The intermediate projection data are in turn compared to the collected projection data to generate error projection data. The error projection data are reconstructed to form an error image. The error image is used to correct the first reconstructed image to form a second reconstructed image. The quality of the second reconstructed image is improved over that of the first reconstructed image.

In a preferred embodiment, reconstruction of the projection data comprises convolution and backprojection of the data. The various steps may be performed over many repetitions to improve image quality at an exponential rate.

The step of comparing the intermediate projection data and the collected projection data preferably comprises subtraction of the corresponding data, as does correction of the reconstructed image by the error image. The spatial resolution of the error projection data may be reduced to improve system performance.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

A. Overview

The magnitude of reconstruction error varies with the cone angle of the X-ray beam and with the technique used for reconstruction. At present, the image quality obtained from a helical cone-beam system having a two-dimensional detector array is significantly inferior to that from a conventional single-row detector system. Although helical cone-beam systems offer a significant advantage in throughput, their applications are limited if the resulting image quality is not comparable to that of the conventional single-row detector system.

The present invention is directed to a technique of mitigating reconstruction error. The technique, referred to herein as successive approximation, is especially attractive for helical cone-beam systems, but is also applicable to other systems where accurate images could not be reconstructed in the prior art. For purposes of the discussion below, a helical cone-beam system will be assumed, i.e. assume conical beams are emitted from a point source to a two-dimensional array of detectors. Assume also that the detector array lies on a cylindrical surface centered about an axis which passes through the source, and that the detector columns lie parallel to the rotation axis, or z-axis, and perpendicular to the xy-plane. The present invention is equally applicable to other conceivable helical scanning geometries, however, for purposes of the following illustration, the foregoing assumptions apply. Note that for purposes of the present invention, the term "channel" refers to a detector channel in a given row of detectors, while the term "column" refers to an arrangement of a column of channels in adjacent detector rows, i.e., along the rotation axis.

Figure 1:
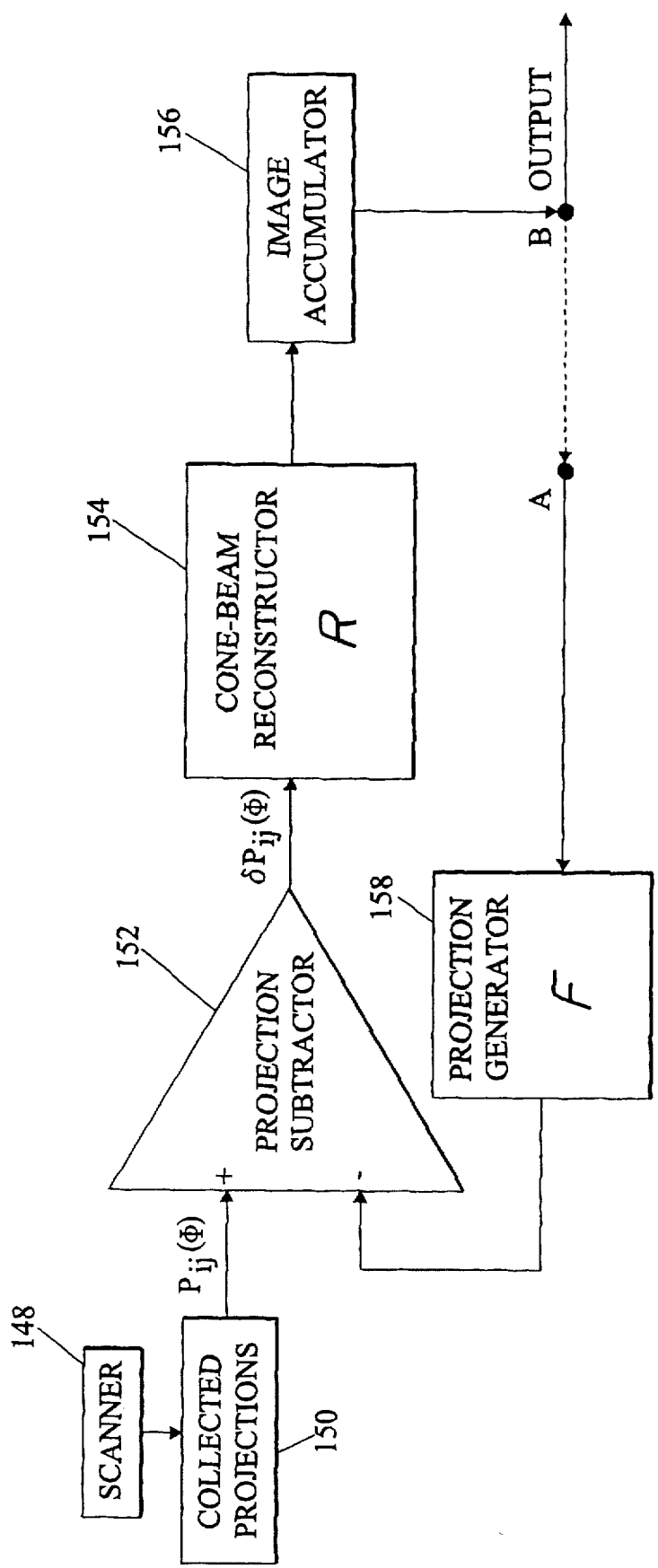
FIG. 1 is a block diagram illustrating the system and the steps involved in the successive approximation technique of computing a volumetric image in a cone-beam computed tomography system, where A is the starting point and B is the finishing point of a first approximation, in accordance with the present invention.
Figure 2:
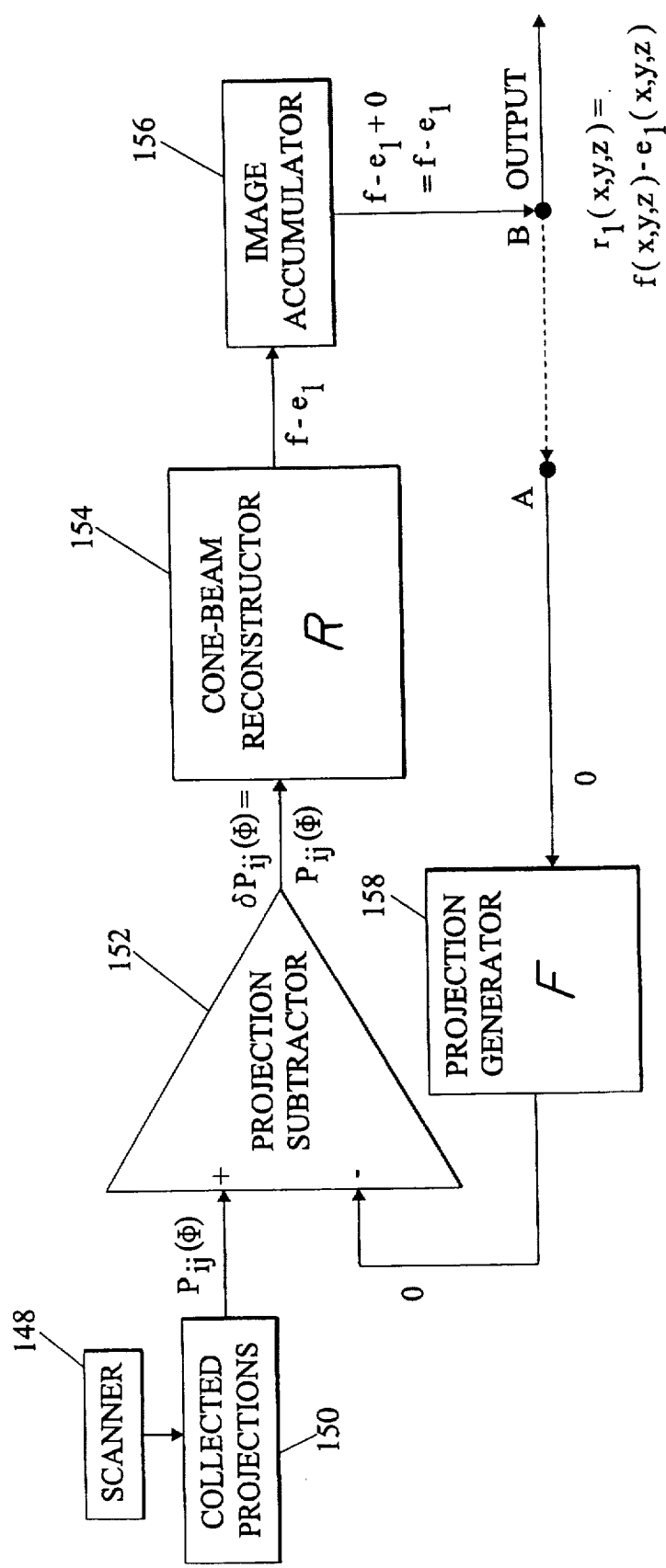
FIG. 2 is a block diagram in accordance with FIG. 1 illustrating the system and the formulation of a first approximation image $r_1(x,y,z)$ from collected projections $P_{ij}(\phi)$.
Figure 3:
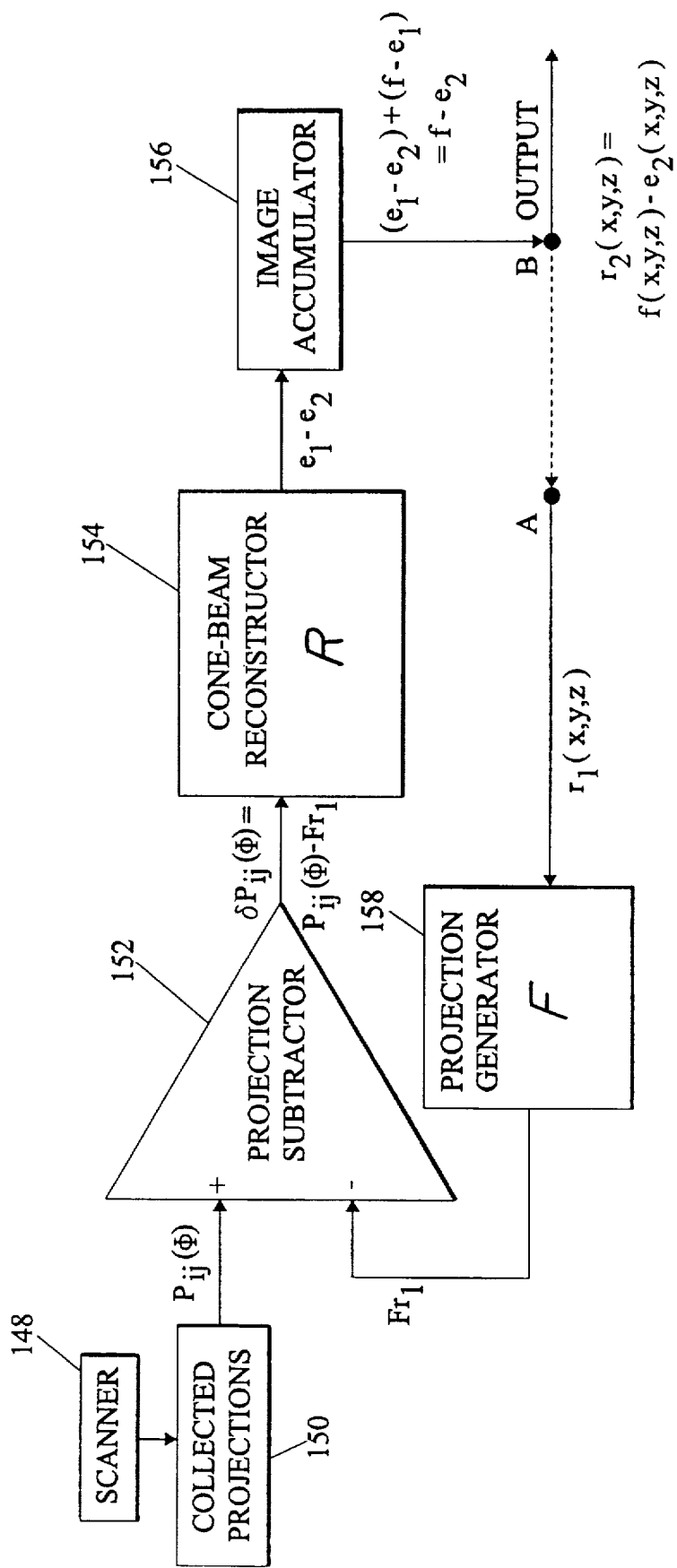
FIG. 3 is a block diagram in accordance with FIG. 1 illustrating the system and the formulation of a second approximation image $r_2(x,y,z)$ from collected projections $P_{ij}(\phi)$ and the first approximation image $r_1(x,y,z)$.
Figure 4:
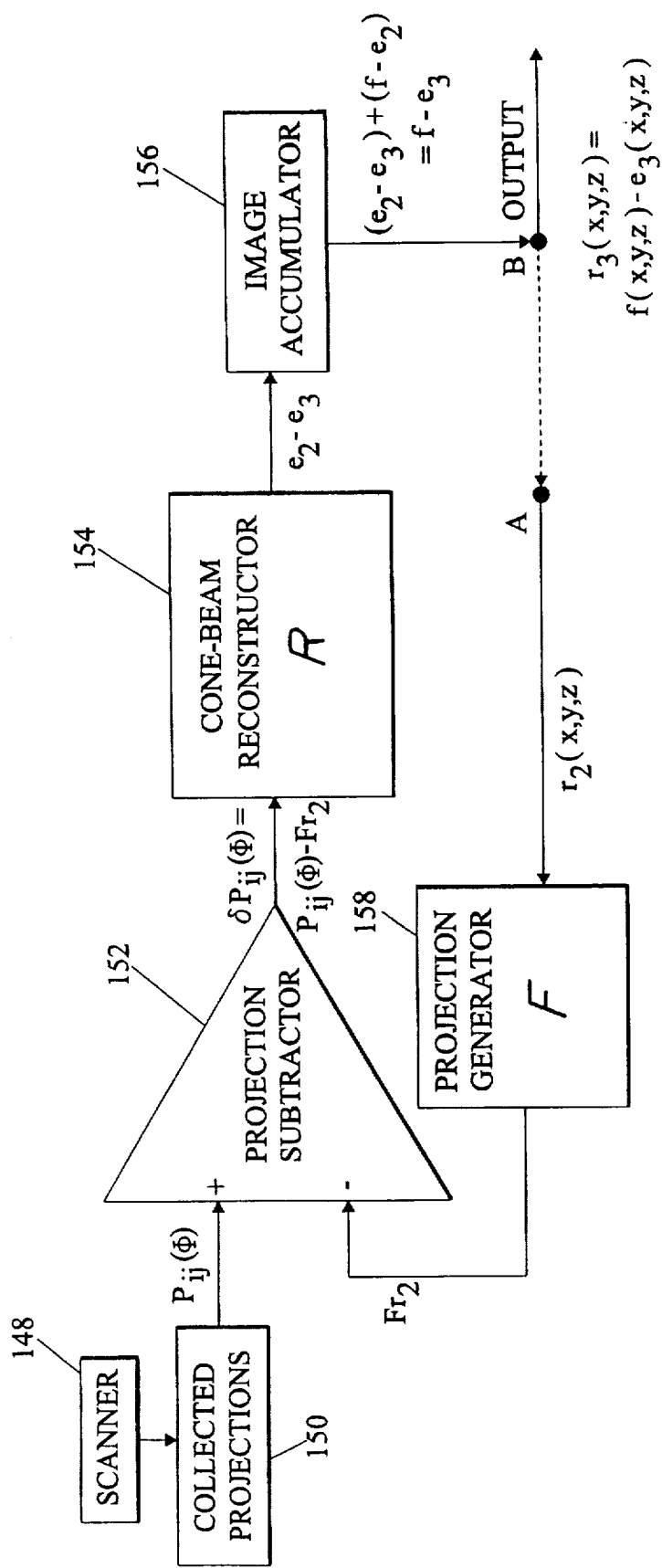
FIG. 4 is a block diagram in accordance with FIG. 1 illustrating the system and the formulation of a third approximation image $r_2(x,y,z)$ from collected projections $P_{ij}(\phi)$ and the second approximation image $r_2(x,y,z)$.

As illustrated in the flow diagram of FIG. 1, in the successive approximation technique of the present invention, an approximate image is first reconstructed at cone-beam reconstructor 154 from projections collected by scanner 148 and stored in data collector 150. The approximate image is stored in an image accumulator 156. The projections of the approximate image in accumulator 156 are regenerated accurately at projection generator 158 and compared with the collected projections $P_{ij}(\phi)$ in collector 150 at projection subtractor 152. A second image is reconstructed at cone-beam reconstructor 154 based on the difference between these two sets of projections. The second image is much smaller than the first image in magnitude and it is used to correct the first image by addition, or alternatively, subtraction, if the error is treated as excessive. By summing the second image and first image, the image accumulator 156 produces a more accurate image of the object, with first-order correction. Further approximation successions result in an increasingly accurate image. The results of each step of the first, second, and third approximations are shown in FIG. 2, FIG. 3, and FIG. 4.

In general, only a small number of iterations are needed for significant improvement in image quality. The optimal number of iterations will depend on the cone angle, the specific reconstruction technique employed, and the accuracy required for the application.

B. Application

In a preferred embodiment, following acquisition of data by the cone-beam scanner 148, the data are converted into projections. The projections can be reordered into parallel projections in xy space and interpolated using the technique of constant-z interpolation as described in U.S. patent application No. 09/038,320, "Method and Apparatus for Reconstructing Volumetric Images in a Helical Scanning Computed Tomography System with Multiple Rows of Detectors," filed Mar. 11, 1998, by the same inventor, referred to hereinafter as the "Lai application", the contents of which are incorporated herein by reference.

For purposes of the present discussion, $P_{ij}(\phi)$ represents the projection value from the jth column and ith row of detectors at view angle $\phi$ after the reordering and preprocessing stages. The projections $P_{ij}(\phi)$ are referred to herein as collected projections which are stored in collector 150, and are used to reconstruct the volumetric image 156 of the object. As described below, the projections $P_{ij}(\phi)$ referred to in FIGS. 1–4 may comprise the originally-collected fan-beam projections $P_{ij}(\theta)$, the reordered parallel-beam projections $R_{ij}(\phi)$, the constant-z interpolated projections $S_{ij}(\phi)$, or, preferably, the projections $T_{ij}(\phi)$ further interpolated to have equal spatial intervals, as described in the above-incorporated Lai application.

Assume there exists an ideal cone-beam reconstruction process which is suited for reconstructing an object image $f(x,y,z)$ from the collected projections $P_{ij}(\phi)$ as accurately as in a conventional CT system. In other words, $f(x,y,z)$ is the ideal volumetric image to be achieved.

The collected projections $P_{ij}(\phi)$ can be considered as the Radon transform, or forward projection, of the ideal volumetric image $f(x,y,z)$. Let F be the operator of such a transform, shown in block 158, such that:

$$P_{ij}(\phi)=Ff(x,y,z) \tag{1}$$

Conversely, the ideal image $f(x,y,z)$ is the inverse transform of $P_{ij}(\phi)$. Let $R_{ideal}$, shown in block 154, be the ideal cone-beam reconstruction operator, which perfectly transforms the collected projections $P_{ij}(\phi)$ back to the ideal image $f(x,y,z)$. That is:

$$f(x,y,z) = R_{ideal} P_{ij}(\phi) \qquad (2)$$

In a real system, the cone-beam reconstruction 154, is able to achieve only approximate results. Assume R to be the operator of the real cone-beam reconstructor 154, and $r_1(x,y,z)$ to be the approximate result. In other words:

$$r_1(x,y,z) = R P_{ij}(\phi) \qquad (3)$$

The result $r_1(x,y,z)$ can be divided into two terms. The first term is the ideal image $f(x,y,z)$, and the second term is the error image $e_1(x,y,z)$ resulting from the approximation in the reconstruction 154. That is, $$r_1(x,y,z) = f(x,y,z) - e_1(x,y,z) \qquad (4)$$

where the voxel value of $e_1(x,y,z)$ can be either positive or negative, and it is treated as the error short of the ideal image value. If $e_1(x,y,z)$ were treated as the error exceeding the ideal image value, Equation (4) would be written as $r_1(x,y,z) = f(x,y,z) + e_1(x,y,z)$. Assuming an appropriate reconstruction technique is employed, the relative magnitude of the values of the data representing the error image $e_1(x,y,z)$ should be much smaller than the corresponding data of the ideal image $f(x,y,z)$. The input data $P_{ij}(\phi)$ and the result of the first approximation $r_i(x,y,z)$ are shown in FIG. 2.

Central to the successive approximation methodology is that, unlike the inverse reconstruction transform R used in convolution and backprojection, the forward transform F used for forward projection in Equation (1) can be computed accurately. Taking the forward transform F of the reconstructed approximate result $r_1(x,y,z)$ of Equation (4) gives:

$$F r_1(x,y,z) = F f(x,y,z) - F e_1(x,y,z) \qquad (5)$$

Let the Radon transform of the error image data be $\delta P_{ij}(\phi)$, that is $$\delta P_{ij}(\phi) = F e_1(x,y,z) \qquad (6)$$

From Equations (1) and (6), Equation (5) becomes $$F r_1(x,y,z) = P_{ij}(\phi) - \delta P_{ij}(\phi) \qquad (7)$$

Equation (7) can be rewritten as:

$$\delta P_{ij}(\phi) = P_{ij}(\phi) - F r_1(x,y,z) \qquad (8)$$

According to Equation (8), the Radon transform of the error image data $\delta P_{ij}(\phi)$ is obtained by subtracting the data representing forward transform F of the first reconstructed image $r_1(x,y,z)$ from the collected projection data $P_{ij}(\phi)$, as shown in FIG. 2.

The forward transform F can be computed by forward-projecting the projections $r_1(x,y,z)$ of the accumulated image 156. The computations should substantially simulate the behavior of the scanner such that within a small tolerance, the projections generated from $f(x,y,z)$ can reproduce the collected projections $P_{ij}(\phi)$.

The computed, forward projected error image projections $\delta P_{ij}(\phi)$ represent fictitious projection data which would produce the error image $e_1(x,y,z)$ if they were reconstructed by an ideal reconstruction technique. Unlike the collected projections $P_{ij}(\phi)$, the values of $\delta P_{ij}(\phi)$ can be positive or negative, and the magnitude is relatively small.

Applying the forward-projected error image $\delta P_{ij}(\phi)$ of Equation (8) to the real cone-beam reconstructor 154, as in equations (3) and (4), gives:

$$R \delta P_{ij}(\phi) = e_1(x,y,z) - e_2(x,y,z) \qquad (9)$$

as illustrated in FIG. 3. As in Equation (4), the second term $e_2(x,y,z)$ represents the associated error in reconstructing the image $e_1(x,y,z)$. The magnitude of the second term $e_2(x,y,z)$ is preferably much smaller than the first term $e_1(x,y,z)$.

In the image accumulator, $R \delta P_{ij}(\phi)$ is added to the first approximation result $r_1(x,y,z)$ to give a second approximation result:

$$r_2(x,y,z) = R \delta P_{ij}(\phi) + r_1(x,y,z) \qquad (10)$$

Using Equations (4) and (9), the second result becomes:

$$r_2(x,y,z) = f(x,y,z) - e_2(x,y,z) \qquad (11)$$

shown at output B of FIG. 3. Equation (11) indicates that $r_2(x,y,z)$ contains only second-order error $e_2(x,y,z)$. As a result, the second reconstructed image $r_2(x,y,z)$ much more closely approximates the ideal image $f(x,y,z)$ than the first reconstructed image $r_1(x,y,z)$, which contains first-order error $e_1(x,y,z)$. The intermediate data and the final result of this second approximation are indicated in FIG. 3. Note that the operation begins at input point A with the first approximation result $r_1(x,y,z)$ as the input, and finishes at the output point B with the second approximation result $r_2(x,y,z)$.

In summary, the present invention employs a closed-loop process to compute data representative of a more accurate second reconstructed image $r_2(x,y,z)$ from the original first reconstructed image $r_1(x,y,z)$. Projections of the first image $r_1(x,y,z)$ are generated and an equivalent projection error $\delta P_{ij}(\phi)$ as expressed in Equation (8) is determined for all view angles. A second image is reconstructed from $\delta P_{ij}(\phi)$ to correct for the first image as given in Equation (10). The above technique can be repeated to compute data representative of a further-improved image $r_3(x,y,z)$ with error $e_3(x,y,z)$ reduced to the third order as shown in FIG. 4. In this case, the second reconstructed image $r_2(x,y,z)$ will be replaced by $r_3(x,y,z)$ and $r_1(x,y,z)$ be replaced by $r_2(x,y,z)$ in the above equations. Equations (8) and (10) therefore become:

$$\delta P_{ij}(\phi) = P_{ij}(\phi) - F r_2(x,y,z) \qquad (12)$$

and $$r_3(x,y,z) = R \delta P_{ij}(\phi) + r_2(x,y,z) \qquad (13)$$

with $$r_3(x,y,z) = f(x,y,z) - e_3(x,y,z) \qquad (14)$$

The input data $r_2(x,y,z)$ at point A, the final result $r_3(x,y,z)$ at point B, and the intermediate data in the operation of this third approximation are shown in FIG. 4. Although these steps can be iteratively repeated to obtain increasingly-improved images, the relative improvement in image quality will level off, or cease, after a certain number of successions. There is a limit to the accuracy that the computer can simulate and generate for the projections. Even with perfect simulation, there are certain inherent errors in the collected projections. When the residual error e(x,y,z) is reduced to the level of the inherent error, no further image improvement will be realized. It is desirable to minimize the number of successions to optimize total computing time.

Let $\int$ be the average magnitude of the data representing the ideal image f(x,y,z), and $e_1$, $e_2$ be the average magnitude of the data representing the error images $e_1(x,y,z)$ and $e_2(x,y,z)$ respectively. The inherent image-to-error ratio can be defined as:

$$C_0 = \int/e_1 \quad (15)$$

which is dependent on the specific reconstruction method used. Likewise, the error reduction rate of the first succession, which produces the second approximation, can be defined as:

$$C_1 = e_1/e_2 \quad (16)$$

The error reduction rate $C_1$ can also be considered as the convergence rate of the successive approximation. If n successions are applied, the final image-to-error ratio C will be the multiple of the convergence rates of each iteration:

$$C = C_0 C_1 \ldots C_n \quad (17)$$

In general, the convergence rate $C_i$ tends to decrease slightly after each succession. That is, $$C_i \leq C_{i-1} \quad (18)$$

where i=1, 2, ..., n, and n is relatively small. For a reconstruction method with $C_i = C_{i-1}$ for all i, the final image-to-error ratio after n successions is $$C_{max} = C_0 C_1 \ldots C_{n} = C_0^{n+1} \quad (19)$$

Equation (19) indicates that in the best case, the image error is reduced exponentially with respect to the number of successions, and $C_0$ is the base of the exponential rate. Thus, the most important factor is the inherent image-to-error ratio $C_0$, which should be as high as possible.

In practice, the improvement in image quality does not track the theoretical exponential rate of image error reduction determined above. This is due to several contributing factors. The convergence rate may be slightly degraded after each succession. If $e_1(x,y,z)$ is more concentrated in small regions than f(x,y,z), the convergence rate of these smaller regions will be lower than other regions. Also, if $e_1(x,y,z)$ is distributed in such a manner that its projections $\delta P_{ij}(\phi)$ are more concentrated in a small number of detector channels or view angles than the collected projections $P_{ij}(\phi)$, the convergence rate will be lower.

In the preferred reconstruction method described in the above-incorporated Lai application, the image error can be considered as the result of the approximation used during convolution. In the frequency domain, the low frequency components of the projections for convolution are less accurate than the high frequency components. The reconstruction error is larger in magnitude in the low frequency components, and the convergence rate $C_1$ is close to $C_0$. Through successive approximation, the error of this reconstruction method is reduced to a negligible level in one or two successions for most applications.

C. Generation of Projections

Ideally, the forward projections created at projection generator 158 are calculated by emulating the data collection system 148, 150 as precisely as possible; however accurate simulation of the scanner 148 is time consuming. For example, the simulation of the X-ray beam shape, the spatial response of each detector, the beam-hardening effect, and so forth, require intensive computations. Thus, for practical reasons, certain approximations are employed in a preferred embodiment of the simulation.

The error of the simulation can be measured by setting the cone angle to zero in the simulator. Projections of an ideal image f(x,y,z) are then generated and used to reconstruct a first ideal image $r_1(x,y,z)$. The ideal image may comprise a composite of two-dimensional images of a conventional scanner or may be created by a computer program. When the cone angle is null, all transaxial fans are parallel to the xy plane. Under this condition, the cone-beam reconstruction, in principle, should produce no error. Projections are generated again from $r_1(x,y,z)$. The discrepancy between the projections of $r_1(x,y,z)$ and projections of f(x,y,z), can be considered as the error of the simulation.

The original projection data in collector 150 and acquired from the scanner are preprocessed to a certain extent before convolution and backprojection. It is not necessary to simulate the projections at this early stage of preprocessing, since they can be computed with high precision. It is the combination of the convolution and backprojection during reconstruction 154 which cause the bulk of the reconstruction error. For this reason, in a preferred embodiment, the simulation needs to generate projections only for convolution and backprojection. The generation of projections at generator 158 is then very much like backprojection, which greatly simplifies the simulation.

During backprojection, the projection path which passes through a voxel at a view angle is first calculated. Since the projection path may not fall exactly into one detector channel, the value for backprojecting to the voxel is interpolated from adjacent channels. For simplicity, consider a system with a single row of detectors. If the projection path of the kth voxel is located at channel position $j_x$ between channels j and j+1, the projection values $P_j$ and $P_{j+1}$ from these two channels will be accumulated into the voxel as $$V_k = V_k + (j+1-j_x)(j_x-j) \cdot P_j +$$

where $$j \leq j_x < j+1. \quad (20)$$

For generating the projections, the channel position $j_x$ is calculated in the same manner as in the backprojection. However, the voxel data value $V_k$ is divided and accumulated into $P_j$ and $P_{j+1}$ as $$P_j = P_j + (j+1-j_x) \cdot V_k$$

$$P_{j+1} = P_{j+1} + (j_x-j) \cdot V_k$$

with $$j \leq j_x < j+1 \quad (21)$$

Equations (20) and (21) characterize the nature of the similarities and differences between backprojection at reconstructor 154 and generation of projections, i.e., forward projections at projection generator 158. Numerical techniques may be used to improve the accuracy and computing speed. Because there are multiple rows of detectors in a cone-beam system, the operations in equations (20) and (21) should therefore be two dimensional.

In the preferred reconstruction method described in the above-incorporated Lai application, the data are reordered into parallel projections in the xy space, and projections from view angles φ are superimposed with those from view angle φ+π for backprojection. Therefore, the projections are preferably generated into the same form of parallel projections for view angles φ and φ+π simultaneously.

Unlike the collected projections $P_{ij}(\phi)$, there is no overlapping region in the generated projections $Fr_1$. Each projection value generated from a projection path is either accumulated into the projection data of view angle φ or the data of view angle φ+π. However, the lack of overlap does not affect the subsequent reconstruction 154. This is because a separation line, as described in the above-incorporated Lai application, is preferably used during reconstruction to divide the projections in the overlapping region into either view angle φ or φ+π. Although the collected data are slightly overlapped, the projections $P_{ij}(\phi)$ introduced to the reconstructor 154 are separated into two non-overlapping regions for backprojection. Thus, by using the separation line, the generated projections $Fr_1(\phi)$ are consistent with the collected projections $P_{ij}(\phi)$ actually used in the backprojection.

As in the backprojection stage of reconstruction, the projection generation at generator 158 is performed in two stages, but in the reverse order of backprojection. Two temporary arrays are preferably used to accumulate projection values for view angles φ and φ+π respectively. If there are m rows in the collected projections per view angle, then m elements are required for each temporary array.

In the first stage, the voxels at the same (x',y') coordinate, but different z' locations, are accumulated in the temporary arrays. The (y,z) coordinate of each voxel with respect to the gantry is calculated in same manner as in the backprojection technique described in the above-incorporated Lai patent application. Depending on whether the z location is greater or less than $z_s$, where $z_s$ is the z coordinate of the separation line, the voxel value is deposited into either array. The exact location on the array, denoted as $i_z$, is calculated in the same manner as in backprojection. As indicated in Equation (21), the voxel is divided and deposited into adjacent elements of either array:

$$T_i = T_i + (i+1-i_z)^* V_{x'y'z'}$$
$$T_{i+1} = T_{i+1} + (i_z-i)^* V_{x'y'z'}$$

where $$i \leq i_z < i+1 \quad (22)$$

and where $T_i$ is ith element of either array. Equation (22) is preferably computed for all z', before progressing to the second stage.

In the second stage, each temporary array is preferably transferred into an accumulative multiple-row projection data array. Based on the x coordinate of these voxels with respect to the gantry, the column number $j_x$ is calculated as in the backprojection. The value in each element of the temporary array, $T_i$, is divided and accumulated into adjacent columns of the corresponding row of the projection data array as:

$$Q_{ij} = Q_{ij} + (j+1-j_x)^* T_i$$
$$Q_{ij+1} = Q_{ij+1} + (j_x-j)^* T_i$$

where $$j \leq j_x < j+1 \text{ and } 0 < i < m \quad (23)$$

and where $Q_{ij}$ is the accumulated projection value for the jth column in the ith row. Equation (23) is computed for both $Q_{ij}(\phi)$ and $Q_{ij}(\phi+\pi)$. The above two-stage operation generates the projection for the voxels with the same (x',y') location. The operation is repeated again to generate the projection for the voxels in the next (x',y') location. When all the voxels from all (x',y') locations have been processed and accumulated into $Q_{ij}$, then $Q_{ij}$ represents the projections of the image at that view angle. That is, $$Q_{ij}(\phi) = P_{ij}(\phi) - \delta P_{ij}(\phi)$$

and $$Q_{ij}(\phi+\pi) = P_{ij}(\phi+\pi) - \delta P_{ij}(\phi+\pi) \quad (24)$$

It may be desirable to apply certain filters to $Q_{ij}$ to make them more compatible with $P_{ij}$, before they are used as $Fr_1(x,y,z)$ in Equation (8).

The procedure described above provides a simple version of the projection generation.

However, it requires a considerable amount of overhead time. This is because the z dimension of the image matrix is relatively short and it happens to be the most iterative dimension in this algorithm. Therefore, as in backprojection, it is preferred to select the x or y dimension as the most iterative dimension, such that the computations can be more efficiently executed by an array processor or a special-purpose computer.

The primary operations in each succession of approximation are generation of projections (forward projection), convolution, and backprojection. The computing time for convolution is relatively small and can be ignored for purposes of the present discussion. The computing time for the other two operations is proportional to the number of voxels and view angles. Therefore, if half spatial resolution is used to generate the projections and reconstruct the error image, the computing time will be highly reduced. At half resolution, the size of both $r_1(x,y,z)$ and $r_2(x,y,z)$ can be reduced from $n_x *n_y *n_z$ to $n_x/2*n_y/2$, which represents a factor of eight in the reduction of the number of pixels. Furthermore, when the image matrix is reduced in the x and y dimensions, the number of view angles become oversampled. Therefore, the number of view angles can also be reduced by a factor of two, resulting in a total reduction of computations by a factor of sixteen.

In a preferred technique, the half spatial resolution applies only to the correction process. The final image is still maintained at full spatial resolution. However, the error image is not corrected to full resolution. After the correction in Equation (11), the resultant image will still contain residual error over the full-resolution frequency range. The magnitude of this residual error is usually small compared to the error being removed, and it depends on the specific reconstruction method. For the preferred reconstruction method described in the above-incorporated Lai application, the error image is the result of low-frequency error in convolution. The error image is in principle at a lower frequency range and hence lower resolution than the ideal image f(x,y,z). Therefore, after reconstructing the first image $r_1(x,y,z)$, it is a favorable strategy to generate the projections and reconstruct the successive images from the error projections $\delta P_{ij}(\phi)$ at half resolution. In this way, the computation time is largely reduced and the final result would be substantially similar in quality to that of the full-resolution correction.

For most applications, retention of accuracy in the z dimension is more important than the x and y dimensions. This is because the z dimension is more prone to reconstruction error as a result of the cone angle, and it is preferred to reconstruct an isotropic volumetric image. It may therefore be desirable to use full resolution in the z dimension and half resolution in the x and y dimensions. In that case, the total reduction factor will be 8, which still amounts to a significant reduction in computing time over a full resolution system.

Assuming that half resolution is employed in the x and y dimensions, the first reconstructed image $r_1(x,y,z)$ will be reduced to $b_1(x,y,z)$ by low pass filtering. A simple way to low-pass filter the data is to use a well-known box-car averaging technique, which gives:

$$b_1(i,j,k)=0.25*(r_1(2i,2j,k)+r_1(2i-1,2j,k)+r_1(2i,2j-1,k)+r_1(2i-1,2j-1,k))$$

with $$i=1,2,\ldots,n_x/2,\ j=1,2,\ldots,n_y/2, k=1,2,\ldots,n_z \quad (25)$$

Based on $b_1(x,y,z)$, the projections $Fb_1(x,y,z)$ are generated at every other view angle. In the meantime, the collected projections $P_{ij}(\phi)$ are also averaged to $$A_{ij}(\phi)=0.25*(P_{i,2j}(\phi)+P_{i,2j}(\phi+\Delta\phi)+P_{i,2j-1}(\phi)+P_{i,2j-1}(\phi+\Delta\phi))$$

with $$i=1,2,\ldots,m,\ j=1,2,\ldots n/2,\ \phi=0,2\Delta\phi,4\Delta\phi,\ldots \pi-2\Delta\phi \quad (26)$$

where n is the number of columns, m in the number of rows of projection data, and $\Delta\phi$ is the increment of the view angle.

The averaging to a smaller number of columns is not necessary, because it would not reduce the subsequent backprojection time. In fact, it is preferred not to average them for better accuracy in reconstruction. In that case, Equation (26) becomes:

$$A_{ij}(\phi)=0.5*(P_{ij}(\phi)+P_{ij}(\phi+\Delta\phi))$$

with $$i=1,2,\ldots,m,\ j=1,2,\ldots,n,\ \phi=0,2\Delta\phi,4\Delta\phi,\ldots \pi-2\Delta\phi \quad (27)$$

The equivalent of Equation (8) in the half resolution correction technique is represented by:

$$\delta A_{ij}(\phi)=A_{ij}(\phi)-Fb_1(x,y,z) \quad (28)$$

As in Equation (9) the error projection data $\delta A_{ij}(\phi)$ are then used to reconstruct the error image at half resolution:

$$R\delta A_{ij}(\phi)=c_1(x,y,z)-c_2(x,y,z) \quad (29)$$

where $c_1(x,y,z)$ and $c_2(x,y,z)$ represent $e_1(x,y,z)$ and $e_2(x,y,z)$ respectively at the reduced matrix size. The half-resolution error image $c_1(x,y,z)-c_2(x,y,z)$ is then expanded to full size by interpolation or duplication for adjacent voxels to $d_1(x,y,z)-d_2(x,y,z)$, with $$d_1(x,y,z)-d_2(x,y,z)\approx e_1(x,y,z)-e_2(x,y,z) \quad (30)$$

With reference to Equation (10), the full-resolution image with second order error becomes:

$$r_2(x,y,z) = r_1(x,y,z) + (d_1(x,y,z) - d_2(x,y,z)) \quad (31)$$
$$\approx r_1(x,y,z) + (e_1(x,y,z) - e_2(x,y,z))$$
or,
$$r_2(x,y,z) \approx f(x,y,z) - e_2(x,y,z)$$

Equations (28) and (31) can be used again for further successions of approximation.

Although a resolution reduction of two is used in the above example, other reduction factors are equally applicable to the present invention. The reduction factor can further be varied in each succession to achieve an optimal correction result in the shortest computing time. For some applications, it may be preferable to use reduced resolution in the early successive approximations including the first image. In that case, the full resolution will be used in a later succession to obtain the final image in full resolution.

D. Conclusion

Although helical cone-beam reconstruction does not provide an exact solution, it is possible to obtain an accurate volumetric image by using the successive approximation technique described above. The improvement in the accuracy of the image in each succession of the approximation depends on the nature of the reconstruction method. If the reconstruction method generates reconstruction error having more uniform spatial distribution and less high-frequency content, then successive approximation will be more effective in improving the image. Given a favorable reconstruction technique, for example the technique described in the above-incorporated Lai application which employs constant-z interpolation, it is possible through successive approximation to achieve the image quality comparable to that of a conventional single-row detector system.

In the preferred cone-beam reconstruction method described in the Lai application, the acquired data projections are accurately reordered and pre-processed before convolution and backprojection. In a preferred embodiment, the projections are generated by generator 158 in form for convolution at reconstructor 154, to simplify the forward projection, and reduce the number of operations. The number of computations for forward projection 158 are similar to the number for backprojection 154 and many of the same computational routines and lookup tables can be used for both operations. By using lower spatial resolution for error correction, the computing time for the successive approximation can be greatly reduced.

Although the successive approximation method presented here pertains to cone-beam reconstruction of helical scans, the technique is equally effective in reducing the cone-beam reconstruction error of stationary (constant z-axis) scans. All equations and procedures presented above are applicable to stationary scans. While this invention has been particularly shown and described with references to preferred embodiments thereof, it will be understood by those skilled in the art that various changes in form and details may be made therein without departing from the spirit and scope of the invention as defined by the appended claims.

I claim:

1. A method of reconstructing an image of an object from collected projection data acquired from a computed tomography system, comprising:

reconstructing the collected projection data to form a first reconstructed image;

forward projecting the first reconstructed image to generate intermediate projection data at multiple view angles;

comparing the intermediate projection data to the collected projection data at the multiple view angles to generate error projection data;

reconstructing the error projection data over the multiple view angles to generate an error image; and correcting the first reconstructed image with the error image to form a second reconstructed image.

2. The method of claim 1, wherein reconstructing forms a volumetric first reconstructed image and wherein correcting forms a volumetric second reconstructed image.

3. The method of claim 1, wherein the computed tomography system is a cone-beam system including a detector array having multiple rows of detectors and further including acquiring the collected projection data using said system.

4. The method of claim 1, wherein the collected projection data are reordered and interpolated data in a form ready for reconstruction.

5. The method of claim 4, wherein the intermediate projection data are generated by forward projecting the first reconstructed image in conformity with the collected projection data ready for reconstruction.

6. The method of claim 1, wherein reconstructing comprises convolving and back projecting the projection data.

7. The method of claim 1, wherein comparing comprises subtracting the intermediate projection data from the collected projection data.

8. The method of claim 1, wherein comparing comprises subtracting the collected projection data from the intermediate projection data.

9. The method of claim 1, further comprising:

forward projecting the second reconstructed image to generate second intermediate projection data;

comparing the second intermediate projection data to the collected projection data to generate second error projection data representative of a reconstructed second error image; and correcting the second reconstructed image with the second error image to form a third reconstructed image.

10. The method of claim 1, wherein the steps of reconstructing, forward projecting, comparing, and correcting are performed in an iterative process of successive approximation such that at each iteration, the error in the reconstructed image decreases.

11. The method of claim 1, wherein correcting comprises summing voxel data representing the error image with corresponding voxel data representing the first reconstructed image.

12. The method of claim 1, wherein correcting comprises subtracting voxel data representing the error image from corresponding voxel data representing the first reconstructed image.

13. The method of claim 1, further comprising filtering the intermediate projection data before comparison with the collected projection data.

14. The method of claim 1, further comprising reducing the spatial resolution of the intermediate projection data during forward projecting of the first reconstructed image for reducing the number of computations.

15. The method of claim 1, further comprising reducing the spatial resolution of the error image under reconstruction for reducing the number of computations.

16. The method of claim 1, further comprising reducing the spatial resolution of the first reconstructed image during reconstruction of the collected projections for reducing the number of computations, and using full spatial resolution during reconstruction of the error projection data.

17. The method of claim 1, further comprising acquiring the collected projection data during a helical scan of the object.

18. The method of claim 1, further comprising acquiring the collected projection data during a constant z-axis scan of the object.

19. The method of claim 1, wherein the collected projection data comprise data selected from the group of data consisting of:

projection data as originally collected by a detector array $P_{ij}(\phi)$, fan-beam projections $P_{ij}(\theta)$, reordered parallel beam projections $R_{ij}(\phi)$, constant-z interpolated projections $S_{ij}(\phi)$, and projection data interpolated to have equal spatial intervals, $T_{ij}(\phi)$.

20. The method of claim 19, wherein forward projecting the first reconstructed image to generate the intermediate projection data includes forward projecting the first reconstructed image in conformity with the collected projections.

21. The method of claim 20, wherein the error projection data representative of reconstructed error image are generated by:

processing the collected projection data and error projection data; and convolving and backprojecting the processed projection data.

22. The method of claim 1 wherein the multiple view angles comprise all view angles of the collected projection data.

23. The method of claim 1 wherein the multiple view angles comprise a subset of the view angles of the collected projection data.

24. A computed tomography system for reconstructing an image of an object from collected projection data, comprising:

means for reconstructing the collected projection data to form data representative of a first reconstructed image;

means for forward projecting the data representative of the first reconstructed image to generate intermediate projection data at multiple view angles;

means for comparing the intermediate projection data to the collected projection data at the multiple view angles to generate error projection data; and means for reconstructing the error projection data over the multiple view angles to generate an error image;

means for correcting the first reconstructed image with the error image to form data representative of a second reconstructed image.

25. The system of claim 24, wherein the collected projection data are reordered and interpolated data in a form ready for reconstruction.

26. The system of claim 25, wherein the intermediate projection data are generated by forward projecting the first reconstructed image in conformity with the collected projection data ready for reconstruction.

27. The system of claim 24, wherein the means for reconstructing comprises means for convolving and means for back projecting the projection data.

28. The system of claim 24, wherein the means for comparing comprises means for subtracting the intermediate projection data from the collected projection data.

29. The system of claim 24, wherein the means for comparing comprises means for subtracting the collected projection data from the intermediate projection data.

30. The system of claim 24, further comprising:
means for forward projecting the second reconstructed image to generate second intermediate projection data;
means for comparing the second intermediate projection data to the collected projection data to generate second error projection data representative of a reconstructed second error image; and
means for correcting the second reconstructed image with the second error image to form a third reconstructed image.

31. The system of claim 24, wherein the means reconstructing, means for forward projecting, means for comparing, and means for correcting operate on the collected data in an iterative process of successive approximation such that at each iteration, the error in the reconstructed image decreases.

32. The system of claim 24, wherein the means for correcting comprises means for summing voxel data representing the error image with corresponding voxel data representing the first reconstructed image.

33. The system of claim 24, wherein the means for correcting comprises means for subtracting voxel data representing the error image from corresponding voxel data representing the first reconstructed image.

34. The system of claim 24, further comprising means for filtering the intermediate projection data before comparison with the collected projection data.

35. The system of claim 24, further comprising means for reducing the spatial resolution of the intermediate projection data during forward projecting of the first reconstructed image for reducing the number of computations.

36. The system of claim 24, further comprising means for reducing the spatial resolution of the error image under reconstruction for reducing the number of computations.

37. The system of claim 24, further comprising means for reducing the spatial resolution of the first reconstructed image during reconstruction of the collected projections for reducing the number of computations, and using full spatial resolution during reconstruction of the error projection data.

38. The system of claim 24, wherein the system comprises a helical scan system.

39. The system of claim 24, wherein the system comprises a constant z-axis scan system.

40. The system of claim 24, wherein the collected projection data comprise data selected from the group of data consisting of:
projection data as originally collected by a detector array $P_{ij}(\phi)$, fan-beam projections $P_{ij}(\theta)$, reordered parallel beam projections $R_{ij}(\phi)$, constant-z interpolated projections $S_{ij}(\phi)$, and projection data interpolated to have equal spatial intervals, $T_{ij}(\phi)$.

41. The system of claim 40, wherein the intermediate projection data are generated by forward projecting the first reconstructed image in conformity with the collected projections.

42. The system of claim 41, further comprising means for reconstructing comprising:
means for processing the collected projection data and error projection data; and
means for convolving and backprojecting the processed projection data.

43. The system of claim 24, further comprising means for reconstructing the error projection data to generate reconstructed error projection data to correct the first error image.

44. The system of claim 24 wherein the multiple view angles comprise all view angles of the collected projection data.

45. The system of claim 24 wherein the multiple view angles comprise a subset of the view angles of the collected projection data.

46. The system of claim 24, wherein the image is volumetric.

47. The system of claim 24, wherein the computed tomography system is a cone-beam system including a detector array having multiple rows of detectors.

48. A method of reconstructing an image of an object from collected projection data acquired from a computed tomography system, comprising:
reconstructing the collected projection data to form a first reconstructed image;
forward projecting the first reconstructed image to generate intermediate projection data;
reducing the spatial resolution of the intermediate projection data;
comparing the intermediate projection data of reduced spatial resolution to the collected projection data to generate error projection data representative of a reconstructed error image; and
correcting the first reconstructed image with the error image to form a second reconstructed image.

49. The method of claim 48 further comprising reducing the spatial resolution of the error image under reconstruction for reducing computations.

50. A method of reconstructing an image of an object from collected projection data acquired from a computed tomography system, comprising:
reconstructing the collected projection data to form a first reconstructed image;
reducing the spatial resolution of the first reconstructed image;
forward projecting the first reconstructed image of reduced spatial resolution to generate intermediate projection data;
comparing the intermediate projection data to the collected projection data to generate error projection data representative of a reconstructed error image; and
correcting the first reconstructed image with the error image to form a second reconstructed image.

51. The method of claim 50 further comprising returning the spatial resolution of the second reconstructed image to the spatial resolution of the collected projection data.

52. A computed tomography system for reconstructing an image of an object from collected projection data, comprising:
means for reconstructing the collected projection data to form data representative of a first reconstructed image;
means for forward projecting the data representative of the first reconstructed image to generate intermediate projection data;
means for reducing the spatial resolution of the intermediate projection data;
means for comparing the intermediate projection data of reduced spatial resolution to the collected projection data to generate error projection data representative of a reconstructed error image;

means for correcting the first reconstructed image with the error projection data to form data representative of a second reconstructed image.

53. The system of claim 52 further comprising means for reducing the spatial resolution of the error image under reconstruction for reducing computations.

54. A computed tomography system for reconstructing an image of an object from collected projection data comprising:
- means for reconstructing the collected projection data to form data representative of a first reconstructed image;
- means for reducing the spatial resolution of the first reconstructed image;
- means for forward projecting the data representative of the first reconstructed image of reduced spatial resolution to generate intermediate projection data; and
- means for comparing the intermediate projection data to the collected projection data to generate error projection data representative of a reconstructed error image;
- means for correcting the first reconstructed image with the error projection data to form data representative of a second reconstructed image.

55. The method of claim 54 further comprising means for returning the spatial resolution of the second reconstructed image to the spatial resolution of the collected projection data.

56. A method of reconstructing an image of an object from collected projection data acquired from a computed tomography system, comprising:
- reconstructing the collected projection data to form a first reconstructed image;
- forward projecting the first reconstructed image to generate intermediate projection data at multiple view angles;
- reconstructing the intermediate projection data over the multiple view angles to generate an intermediate image;
- comparing the intermediate image to the first reconstructed image to generate an error image; and
- correcting the first reconstructed image with the error image to form a second reconstructed image.

57. A computed tomography system for reconstructing an image of an object from collected projection data; comprising:
- means for reconstructing the collected projection data to form data representative of a first reconstructed image;
- means for forward projecting the data representative of the first reconstructed image to generate intermediate projection data at multiple view angles;
- means for reconstructing the intermediate projection data over the multiple view angles to generate an intermediate image;
- means for comparing the intermediate image to the first reconstructed image to generate an error image; and
- means for correcting the first reconstructed image with the error image to form a second reconstructed image.

* * * * *